(12) United States Patent
Ott et al.

(10) Patent No.: US 8,932,248 B2
(45) Date of Patent: Jan. 13, 2015

(54) GAS CONDITIONING TROCARS

(75) Inventors: Douglas E. Ott, Macon, GA (US); Duane Lloyd, Glasgow, MT (US)

(73) Assignee: Lexion Medical LLC, St. Paul, MN (US)

(*) Notice: Subject to any disclaimer, the term of this patent is extended or adjusted under 35 U.S.C. 154(b) by 560 days.

(21) Appl. No.: 12/381,978

(22) Filed: Mar. 18, 2009

(65) Prior Publication Data

US 2010/0241061 A1    Sep. 23, 2010

(51) Int. Cl.
A61M 37/00 (2006.01)
A61M 13/00 (2006.01)
A61B 17/34 (2006.01)

(52) U.S. Cl.
CPC .......... *A61M 13/003* (2013.01); *A61B 17/3474* (2013.01); *A61M 2205/3372* (2013.01); *A61M 2205/3653* (2013.01)
USPC .......................................................... 604/26

(58) Field of Classification Search
USPC ................... 604/23–26, 264, 164.01–164.09
See application file for complete search history.

(56) References Cited

U.S. PATENT DOCUMENTS

| | | | |
|---|---|---|---|
| 5,411,474 A * | 5/1995 | Ott et al. | 604/26 |
| 6,010,118 A * | 1/2000 | Milewicz | 261/142 |
| 6,685,665 B2 * | 2/2004 | Booth et al. | 604/26 |
| 6,797,167 B2 * | 9/2004 | Koslow | 210/493.1 |
| 6,814,714 B1 | 11/2004 | Novak et al. | |
| 2004/0102731 A1 * | 5/2004 | Blackhurst et al. | 604/26 |
| 2005/0113797 A1 | 5/2005 | Ott et al. | |
| 2006/0129098 A1 * | 6/2006 | Hart et al. | 604/113 |
| 2006/0184096 A1 * | 8/2006 | Ott et al. | 604/26 |
| 2007/0088274 A1 * | 4/2007 | Stubbs et al. | 604/164.01 |
| 2007/0088275 A1 | 4/2007 | Stearns et al. | |
| 2012/0245509 A1 * | 9/2012 | Tran et al. | 604/24 |

* cited by examiner

*Primary Examiner* — Quynh-Nhu H Vu
*Assistant Examiner* — Brandy S Lee
(74) *Attorney, Agent, or Firm* — Jacobson & Johnson LLC

(57) ABSTRACT

A gas conditioning trocar having a chamber for heating and hydrating an unconditioned insufflation gas prior to injecting a conditioned insufflation gas into a body cavity during a medical procedure and a port through which surgical instruments can pass into a body cavity without inhibiting the flow of insufflation gas during the medical procedure.

13 Claims, 2 Drawing Sheets

GAS CONDITIONING TROCARS

FIELD OF THE INVENTION

This invention relates to the field of medical devices and more specifically to a gas conditioning trocar for heating and/or hydrating an insufflation gas during a medical procedure.

BACKGROUND OF THE INVENTION

The concept of a medical apparatus for humidifying or otherwise treating a gas from an insufflator during surgery is described in Douglas Ott et al. U.S. Pat. Nos. 5,411,474; 6,068,609 and 7,066,902. Briefly, an insufflation gas is heated and hydrated i.e. conditioned, before the gas is directed into a body cavity through a device such as a trocar. In order to hydrate the insufflation gas a charge of hydration fluid is typically injected into a device where the hydration fluid can humidify the insufflation gas and a heater can bring the insufflation gas to a temperature near body temperature. The conditioned insufflation gas is then sent to a trocar for injection into a body cavity of a patient.

BRIEF SUMMARY OF THE INVENTION

Briefly, the invention comprises a gas conditioning trocar for on-the-go heating and/or hydrating of an insufflation gas immediately prior to its use in a medical procedure while allowing use of the trocar for insertion of medical instruments therein.

The invention has several important technical advantages. Embodiments of the invention may have none, some, or all of these advantages.

The invention includes the ability to heat insufflation gas immediately prior to injecting the insufflation gas thereby minimizing heat losses after the insulation gas has been heated.

The invention includes the ability to hydrate the insufflation gas immediately prior to injecting the insufflation gas thereby minimizing condensation after the insufflation gas has been humidified.

A further advantage is that the hydration unit and the trocar form a compact easy to use disposable unit.

DESCRIPTION OF THE PREFERRED EMBODIMENT

Figure 1:
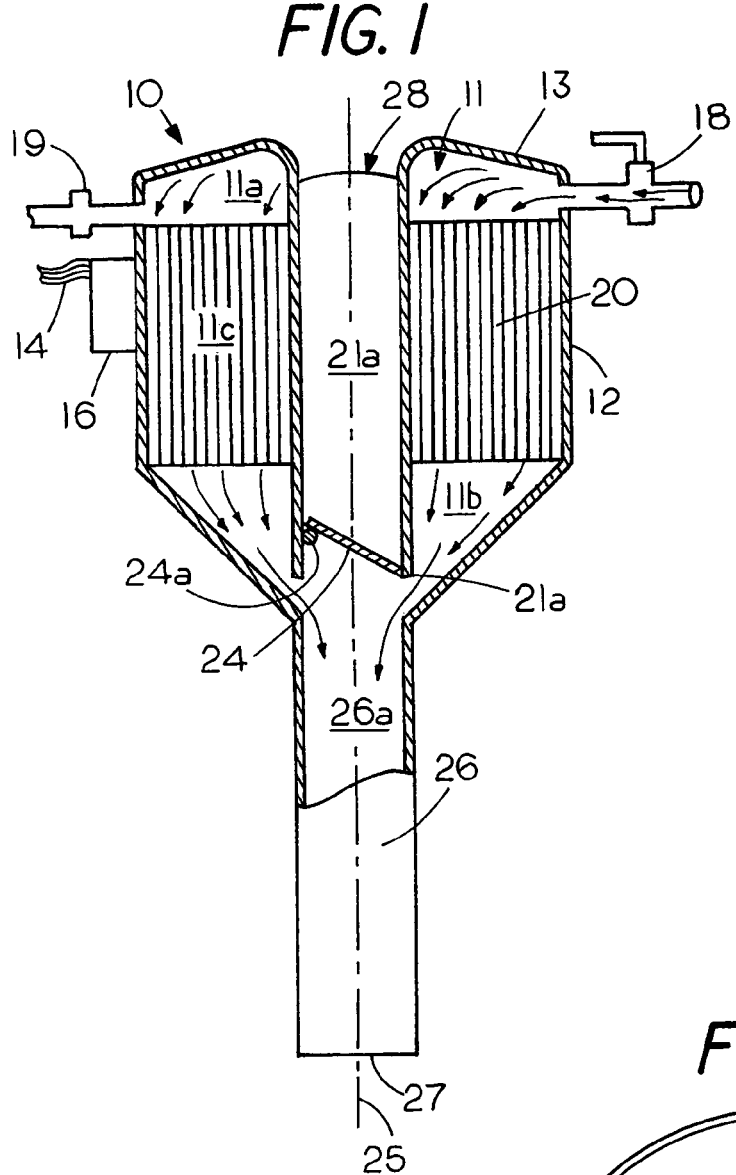
FIG. 1 is a side partial sectional view of the trocar.

FIG. 1 shows a partial cut away side view of a gas conditioning trocar for on-the-go heating and/or hydrating of an insufflation gas during a medical procedure. Trocar 10 includes a cylindrical housing 12 having a cannula 26 on one end and a cover 13 on the opposite end. The cannula 26 comprises an elongated cylindrical tube for extending into a patient's body cavity. While not explicitly shown, cannula 26 may include a sharp member for piercing the skin and tissue between the skin and the peritoneal cavity. Such a member may be spring loaded and may take many different forms as understood by persons skilled in the art. Any form of a sharp member may be used or the sharp member omitted without departing from the scope of the invention.

Cylindrical housing 12 and an upper coaxial tube 21 form an annular chamber 11 within trocar 10. Chamber 11 could have another shape without departing from the scope of the invention. Annular chamber 11 comprises three parts, an upper annular plenum chamber 11a where insufflation fluids and insulation gas are introduced, a central annular chamber 11c, which may contain a conditioning media 20 for transporting the insufflation gas and/or a hydration fluid threrethrough while bringing the insufflation gas to a conditioned state as it enters the lower annular plenum chamber 11b. From plenum chamber 11b the conditioned insufflation gas flows into cannula 26 through an annular outlet port 21a.

Connected to one side of housing 12 may be a valve 18 for controlling the flow of insufflation gas into upper annular plenum chamber 11a and similarly connected to the opposite side of housing 12 may be a further valve 19, which may be a check valve, to control the flow of hydration fluids into housing 12 as well as to prevent backflow of hydration fluids. While mechanical valves are shown other types of controls may be used; for example, fluidic controls may be used to control the delivery of fluids to the gas conditioning trocar. Either valve 19 or valve 18 or both may be omitted without departing from the scope of the invention. The invention also includes trocars with multiple ports into housing 12 where flow of gases and fluids into such ports is controlled by valves in tubing leading to such ports. In this embodiment, junction box 16 is mounted on the side of housing 12 and contains electrical leads 14 from a heater located in the conditioning media 20. Junction box 16 can be omitted without departing from the scope of the invention. In some embodiments, the heater may be omitted. In other embodiments, conditioning media 20 may be omitted. Typically, the hydration fluid may be water, however, other fluids may be included in addition to or instead of the water. For example, a saline solution, an anesthetic, an antibiotic, or other pharmacologic agent could be used.

As used herein, the term "agent" means any organic substance, inorganic substance, inert or biologically active substance of pharmacologic material, that may effect or enhance tissue healing, reduce infection, reduce adhesions formation, modify the immunologic response, treat specific disease processes, reduce pain or be used for any therapeutic or diagnostic purpose. This includes materials in solid, liquid or gas phase, and materials that are water (aqueous) based, colloid and non-colloid suspensions, mixtures, solutions, hydrogels, lypholized materials, hydrophobic, hydrophilic, anionic, cationic, surface active agents, surgical adjuvants, anticoagulants, antibiotics, immunologic stimulators, immunologic suppressants, growth inhibitors, growth stimulators, diagnostic materials, anesthetic agents, analgesic agents, and materials by themselves or dissolved or based in other materials, such as, but not limited to, alcohols, ethers, esters, lipids and solvents. The agent can be dry, such as in a power form. Any material that can be carried by the flow of gas into a body cavity or onto a surface for therapeutic or diagnostic purposes can be delivered in accordance with this invention. It is not intended to limit the present invention to the above examples of agents. Furthermore, the gas stream may be treated with any type or combination of agents in accordance with the present invention. An example is to treat the gas stream with a humidifying solution for hydration to prevent desiccation, an antibiotic to reduce infection, an anti-inflammatory to reduce inflammation and an anti-adhesive to reduce adhesions and improve healing. Agents such as those sold under the trademarks Adept manufactured by ML Laboratories, Adcon manufactured by Gliatech and Atrisol manufactured by Atrix Laboratories can be used to reduce adhesions.

While in this embodiment, hydration fluids enter through valve 19, the trocar could be packaged in a precharged condition with fluid contained in chamber 11c. A recharge port could also be included in tubing leading to the trocar or placed anywhere on the trocar body such that a fluid can reach chamber 11c.

In the illustrated embodiment, conditioning media contains both a heater and a porous material capable of absorbing water. In operation of this embodiment of gas conditioning trocar 10, the insufflation gas and the hydration fluids are introduced into plenum chamber 11a and flow in an axial direction through the conditioning media 20 in chamber 11c where the insufflation gas may be hydrated and heated to a temperature near body temperature for injection into the body cavity of a patient. As the insufflation gas and hydration fluids flow through the conditioning media 20, the conditioning media 20 allows the insufflation gas to be hydrated and/or heated immediately prior to injection of the insufflation gas into the body cavity of a patient thus avoiding transport loses that may occur with remote hydration units. A portion of cannula 26 is typically inserted into a body cavity.

The conditioned insufflation gas flows from lower plenum chamber 11b into passage 26 through annular inlet port 21a. A surgical instrument may be passed through instrument inlet 28, into passage 21a and, through cannula 26 and out the end 27 of cannula 26. The instrument may be withdrawn and other instruments may be used in a similar fashion throughout the procedure. As such, the delivery of conditioned insufflation gas and the use of surgical instruments may occur simultaneously without adversely affecting or interfering with each other.

In some embodiments, the insufflation gas may only be hydrated and the heater in conditioning media can be omitted. In other embodiments, the insufflation gas may only be heated and the conditioning media 20 may be omitted. In other embodiments, a material capable of filtering insufflation gas may be used as conditioning media 20 with or without a heater. Thus, the invention further includes a trocar 10 with only an insufflation gas filter in cavity 11c.

Figure 2:
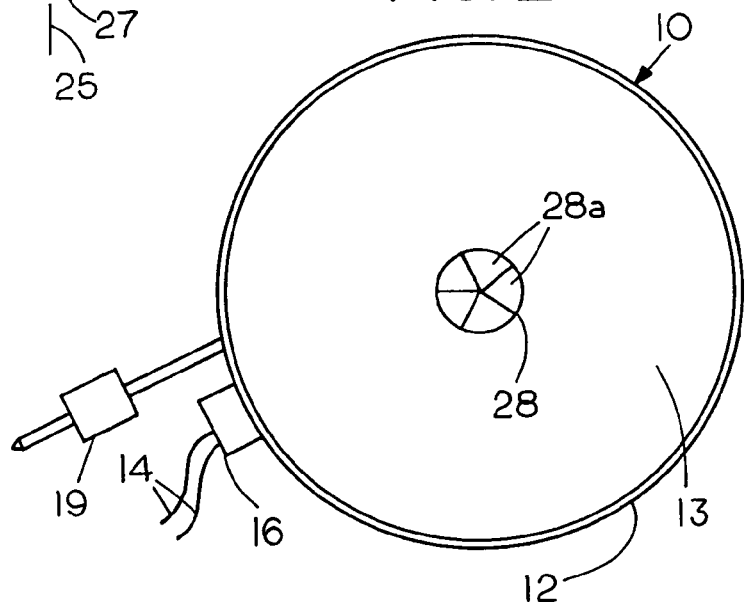
FIG. 2 is a top view of the trocar housing cover.

FIG. 2 shows a top view of the trocar housing 12 revealing an inlet instrument port 28, which is located in the center of housing 12. In this embodiment, extending across instrument port 28 is a closure comprising a plurality of segment shaped resilient flaps 28a that normally extend radially inward in tube 21 to block passage 21a and thereby inhibit or prevent backflow of insufflation gas therepast whether or not a surgical instrument is present in trocar 10. The closure may comprise a duckbill opening or lever valve. When a surgical instrument is inserted into trocar 10 the flaps 28a flex to allow the instrument to enter and pass through passage 21a in tube 21. Preferably, the flaps 28a are made of a resilient material such that they form a gas seal around the exterior surface of the surgical instrument therein to inhibit or prevent insufflation gas from escaping therepast when the surgical instrument is located in trocar 10. If the surgical instrument is withdrawn from tube 21, then the flaps 28a return to the closed condition shown in FIG. 1 to inhibit or prevent insufflation gas (e.g., conditioned gas) from escaping through instrument inlet port 28. A further benefit is that the flaps 28a may prevent contaminants from inadvertently entering trocar 10. While resilient flaps are shown comprising the closure other methods and means may be used to close off the instrument port to inhibit or prevent backflow of insufflation gas therepast. Any technique for doing so may be used without departing from the scope of the invention.

In the example shown the on-the-go and in situ heating and hydrating of the insulation gas takes place in conditioning media 20 which is located in the annular chamber in the gas conditioning trocar 10.

Figure 3:
FIG. 3 is a side view of a multilayer media in an unwound condition.

FIG. 3 shows a side view of an example of a strip of a conditioning media 20 for bringing an insufflation gas into a conditioned state. Media 20 comprises multiple layers i.e. a multilayer media, in an unwound or unassembled condition. In the example shown the materials of multilayer media 20 include a layer of gas transfer material comprising netting 32 and a layer of a fluid transferring material comprising hydrophilic material 30 with a heater assembly 34 extending therebetween. Heater assembly 34 includes a temperature sensor 22 on one end and a pair of electrical leads 14 on the opposite end for connection to a power source. Although three layers are shown the number and composition of the layers of material as well as the thickness of the layers may be modified according to the specific application. Temperature sensor 22 may be part of heater assembly 34 or may be separately mounted in trocar 20 to monitor the temperature of the heater or of the insufflation gas before the insufflation gas is discharged from the trocar 20. Additional temperature sensors 22 may be included and control circuitry to control the heater such that the insufflation gas temperature is maintained within a temperature range may be located within junction box 16 or remotely from the heater assembly 34 and temperature sensors.

One or all of the above components can be omitted from conditioning media without departing from the scope of the invention. As noted above, some embodiments may have a filtering media, some may omit the heater, and some may include only a heater and no other media. Any arrangement of the heater, temperature sensor and absorbent material may be used without departing from the scope of the invention. The media may be arranged to allow gas to primarily flow over or primarily flow through the media. The heater may be located in chamber 11c or in any other chamber of trocar 10 where the insufflation gas can be treated. Preferably, the gas will be heated substantially simultaneously as shown but could be heated and humidified separately.

Figure 4:
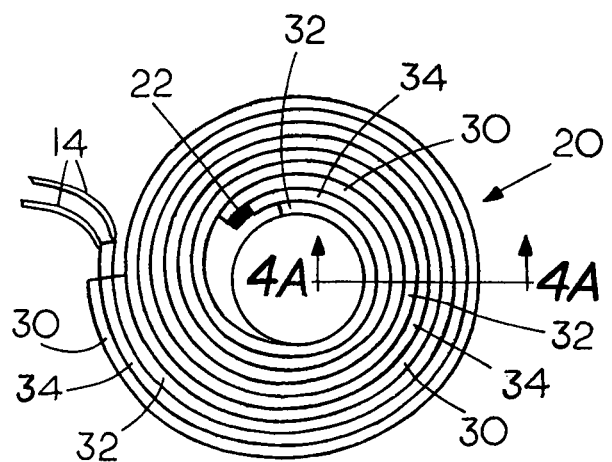
FIG. 4 is top view of the multilayer media arranged in a spiral configuration.

FIG. 4 shows the example strip of multilayer media 20 comprises a plurality of three layers of materials 30, 32 and 34 which may be wound into a spiral configuration that may be inserted into the annular chamber in trocar 10. In the spiral configuration state, as shown in FIG. 4, the hydrating liquid may be brought into proximity of a heater assembly 34 through an absorbing action of a hydrophilic layer 30 in media 20. The absorbing action allows distribution of the hydrating liquid proximate the heater assembly 34. Similarly, a porous netting 32 may allow the insufflation gas to flow threrethrough so the gas can be brought into proximity of the heater assembly 34 to enable the insufflation gas to be brought to a conditioned state.

Figure 4A:
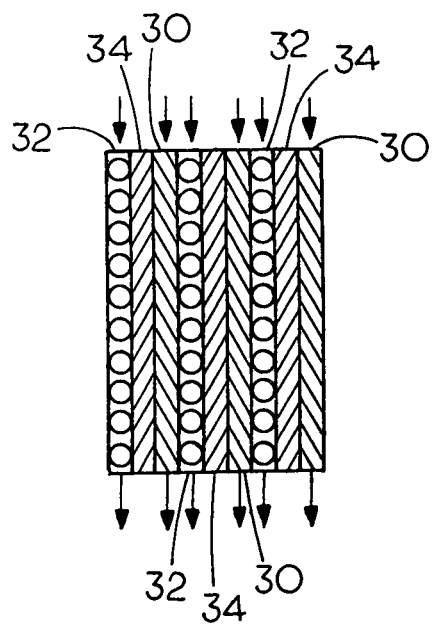
FIG. 4A is a cross sectional view taken along lines 4A-4A of FIG. 4.

FIG. 4A is a cross sectional view of the spirally wound media 20 taken along lines 4A-4A of FIG. 4 revealing the multiple layers comprising the conditioned media 20.

In order to secure the multilayer media 20 in the housing 12 the multilayer media 20 may be wound into a diameter slightly larger than the diameter of housing 12 to enable one to friction fit multilayer media 20 in housing 12. If frictional forces are used to hold multilayer media 20, then the multilayer media should be selected to offer sufficiently low flow resistance so that the insufflation gas flow flowing thereto will not displace the multilayer media 20.

Alternatively, multilayer media 20 could be adhesively secured to housing 12. It is noted that an advantage of the friction fit of multilayer media 20 in housing 12 is that the friction fit reduces the need for an adhesive to hold multilayer media 20 in place. An adhesive may interfere with the flow of insufflation gas from one layer of multilayer media 20 to another. An alternate method of holding the multilayer media 20 in position may be to use a radial supports in chamber 11b to support the lower end of multilayer media 20. Other methods of securing the multilayer media 20 may also be used to maintain the multilayer media 20 in position to deliver hydrated insufflation gas to annular outlet port 21a.

To decrease the pressure drop through netting 32 two or more layers of netting may be placed proximate each other to increase the porosity though the netting. That is, netting 32 provides flow passages for the insufflation gas to flow from plenum chamber 11a to plenum chamber 11b without undue but sufficient resistance so that the hydration fluid and the hydration gas can be maintained in proximity to enable hydration to take place in embodiments where hydration is performed. A suitable netting 32, for example, is a bi-planar polypropylene netting having properties including a density of 11 strands per inch and a thickness of 0.030 inches (e.g., Delstar, Middleton, Del.). Any netting capable of allowing gas flow could be used without departing from the scope of the invention. Also, the netting 32 could be omitted.

Multilayer media 20 may include at least one layer of a liquid transfer media, which for example may be a hydrophilic media 30, that readily absorbs and retains a volume of hydration fluid provided to plenum chamber 11a. While other types of materials, for example wicking materials, may be used to deliver the hydration fluid into proximity of the heater assembly 34, the hydrophilic media 30 may bring the hydration fluid in close proximity to both heater assembly 34 and the insufflation gas through an absorbing action. Similarly, two or more layers of hydrophilic material may be used to bring the hydration liquid proximate the heater assembly.

Hydrophilic media 30 may be thin and flexible so that it is easily wound in a spiral configuration with the other layers of multilayer media 20 as shown in FIG. 4. Although many types of hydrophilic material are useable, a typical suitable hydrophilic media 30 is cellulose which is commercially available from Knowlton, Watertown, N.Y. having the following characteristics: a basis weight of 91-99 pounds/3000 $ft^2$ and a thickness of about 0.028-0.034 inches.

The multilayer media 20 may include a heater assembly 34, which may comprise an elongated flexible heating element that has external electrical leads 44 for connecting to a source of electrical power. The heater assembly 34 may be thin and flexible such that when it is sandwiched between the hydrophilic layer 30 and the layer of netting 32 the combination can be wound into a spiral configuration that can be inserted within housing 12. An advantage of the spiraled configuration is that it provides a continuous extended area for heating and hydration of the insufflation gas, i.e., the insufflation flow path is long. In the preferred embodiment, heater assembly 34, for example, is a resistance heating element made of etched copper foil coated with a layer of polyimide. Another layer of polyimide may coat the foil surface. The coating of polyimide reduces the likelihood of heater assembly 34 from contacting the hydration fluid or hydrated gas such that an electrical short results. As discussed above, however, any type of heater and any type of absorbent material may be used with the invention.

One end of heater assembly 34 may terminate with a temperature sensor 22 for measuring the temperature of the heater in the gas conditioning trocar 10. In other embodiments, multiple temperature sensors may be used and may be located elsewhere to sense the temperature of the gas directly rather than sensing the temperature of the heater. The temperature sensor can be located in one of the chambers 11b or 11c or located in the cannula 26. In some cases, a remote sensor (e.g. an electronic infrared sensor) exterior to the trocar could be used. When heater assembly 34 is layered with the other materials of multilayer media 20 and friction fit into housing 12, temperature sensor 22, for example a thermistor, detects the temperature of the heater at lower plenum chamber 11b. A heater control, not shown, can increase or decrease the power supplied to heater assembly 34 to maintain the temperature within a desirable range for injection into a body cavity. The opposite end of heater assembly 34 may terminate with electrical leads 14 which can be connected to a power source. When heater assembly 34 is layered with netting 32 and hydrophilic media 30 and assembled into a spiral configuration, electrical leads 14 may extend beyond the multilayer media 20. Thus, when the multilayer media 20 is placed in housing 12, the electrical leads 14 may extend beyond housing 12 for connection to a source of electrical power as shown in FIG. 1.

In the preferred embodiment, multilayer media 20 is assembled into a spiral configuration (FIG. 4) although other configurations may be used. An advantage of the spiral configuration is that the hydrating fluid and insufflation gas are brought in to close proximity to the heater assembly 34 as they flow from annular plenum chamber 11a to annular plenum chamber 11b. Although an annular conditioning media 20 which extends from side to side is shown, the gas conditioning media may take other shapes or forms which allow the insufflation gas to be conditioned within the trocar. For example, only a portion of the annular chamber in the trocar may be used for the conditioning of the gas. A further benefit and advantage of use of a multilayer media is that multilayer media 20 can more easily be assembled in a flat condition and subsequently wound into a spiral configuration for insertion into the annular chamber of the trocar 10.

Referring to FIG. 1, an elongated cylindrical passages 21a and 26a extend along a central axis 25 of trocar 10. Passages 21a and 26a are of adequate diameter to simultaneously house a surgical instrument and allow a flow insufflation gas without undue fluid resistance thereto.

Trocar 10 may include a closure such as a hinged flap 24, which is normally held in a closed position by a spring 24a to prevent backflow of bodily fluids or other materials from the patient's body cavity. Flap 24 opens in response to a medical instrument being inserted into passages 26a. It is noted that while flap 24 is the preferred embodiment, other methods or structures may be used to prevent backflow.

We claim:

1. A gas conditioning trocar for use during a medical procedure comprising:

a housing having an instrument passage for insertion of a surgical instrument therein;

an annular chamber located in said housing;

an annular inlet plenum chamber located in a first portion of said chamber for receiving an unconditioned insufflation gas;

an annular outlet plenum chamber located in a further portion of said chamber for receiving a heated and hydrated insufflation gas;

a cannula for insertion into a body cavity wherein the instrument passage extends through the annular chamber and the cannula; and a spiral wound conditioning media comprising a plurality of layers of materials with a one of the plurality of layers of materials carrying a hydration fluid therein, said spiral wound gas conditioning media located within said annular chamber and between said annular inlet plenum chamber and said annular outlet plenum chamber with a first end of the spiral wound conditioning media in fluid communication with the annular inlet plenum chamber and an opposite end of the spiral wound conditioning media in fluid communication with the annular outlet plenum chamber thereby forming an end to end insufflation gas flow path from an end of the spiral wound conditioning media in the inlet plenum chamber to an opposite end of the spiral wound media in the outlet plenum chamber wherein the insufflation gas flows between and along the plurality of layers of materials of the conditioning media located in the annular chamber as the conditioning media hydrates the insufflation gas by absorbing the hydration fluid into the insufflation gas as the insufflation gas flows alongside the one of the plurality of layers of materials carrying the hydration fluid, said spiral wound conditioning media including an electrical heater with the insufflation gas flow path located on opposite sides of the electrical heater for heating the insufflation gas within the spiral wound conditioning media before delivery of the heated and hydrated insufflation gas to a body cavity of a patient.

2. The gas conditioning trocar of claim 1 including a temperature sensor located within the chamber to monitor the temperature of the insufflation gas.

3. The gas conditioning trocar of claim 2 wherein the temperature sensor comprises a thermistor.

4. The gas conditioning trocar of claim 1 wherein the conditioning media comprises a multilayer media comprising a hydrophilic layer and a layer of netting.

5. The gas conditioning trocar of claim 4 wherein the media is maintained in the chamber through a friction fit within the housing.

6. The gas conditioning trocar of claim 4 wherein the hydrophilic layer comprises cellulose.

7. The gas conditioning trocar of claim 4 wherein the netting comprises polypropylene.

8. The gas conditioning trocar of claim 4 wherein the netting comprises a bi-planar netting.

9. The gas conditioning trocar of claim 1 wherein the electrical heater comprises a resistance heating element.

10. The gas conditioning trocar of claim 9 wherein the resistance heating element comprises an etched copper foil coated with a layer of polyimide.

11. The gas conditioning trocar of claim 9 wherein the resistance heating element comprises an etched copper foil.

12. The gas conditioning trocar of claim 1, further comprising a closure that extends across the instrument port with the closure sealing against a surgical instrument extending through the instrument port to inhibit loss of the insufflation gas.

13. The gas conditioning trocar of claim 12 wherein the closure comprises a plurality of flaps that remain closed when the instrument passage is vacant.

* * * * *